United States Patent
Ibrahim (10) Patent No.: US 7,860,572 B2
(45) Date of Patent: Dec. 28, 2010

(54) METHOD FOR CONDUCTING SIGNALS IN A MEDICAL DEVICE

(75) Inventor: Ibrahim Ibrahim, North Ryde (AU)

(73) Assignee: Cochlear Limited, Lane Cove (AU)

( * ) Notice: Subject to any disclaimer, the term of this patent is extended or adjusted under 35 U.S.C. 154(b) by 245 days.

(21) Appl. No.: 10/887,894

(22) Filed: Jul. 12, 2004

(65) Prior Publication Data

US 2005/0010267 A1 Jan. 13, 2005

(30) Foreign Application Priority Data

Jul. 11, 2003 (AU) .............................. 2003903579

(51) Int. Cl.
*A61N 1/372* (2006.01)
(52) U.S. Cl. .......................................... 607/57; 607/61
(58) Field of Classification Search ................... 607/37, 607/55–57, 59–61
See application file for complete search history.

(56) References Cited

U.S. PATENT DOCUMENTS

| | | | |
|---|---|---|---|
| 3,299,390 A | 1/1967 | Eckelkamp | |
| 4,532,930 A * | 8/1985 | Crosby et al. | 607/57 |
| 5,042,084 A * | 8/1991 | Daly | 455/41.1 |
| 5,646,368 A | 7/1997 | Muyshondt et al. | |
| 5,966,056 A | 10/1999 | Thornton | |
| 6,115,636 A | 9/2000 | Ryan | |
| 6,231,604 B1 * | 5/2001 | von Ilberg | 623/10 |
| 6,308,101 B1 * | 10/2001 | Faltys et al. | 607/57 |
| 6,498,300 B2 | 12/2002 | Flick | |
| 6,537,200 B2 | 3/2003 | Leysieffer et al. | |
| 6,565,503 B2 | 5/2003 | Leysieffer et al. | |
| 6,575,894 B2 | 6/2003 | Leysieffer et al. | |
| 6,697,674 B2 | 2/2004 | Leysieffer | |
| 2006/0046766 A1 | 3/2006 | Hair et al. | |

* cited by examiner

*Primary Examiner*—Eric D. Bertram
(74) *Attorney, Agent, or Firm*—Kilpatrick Stockton LLP (57) ABSTRACT

In accordance with one aspect of the present invention, a cable for communicably connecting a first component and a second component of a cochlear implant system is disclosed. The cable comprises: a first conductor for conducting at least one analog-domain signal; a second conductor for conducting at least one digital-domain signal; and at least one ground conductor electrically coupled to the first and second conductors.

27 Claims, 5 Drawing Sheets

METHOD FOR CONDUCTING SIGNALS IN A MEDICAL DEVICE

CROSS-REFERENCE TO RELATED APPLICATIONS

This application claims the priority of co-pending Australian Pat. No. 2003903579, entitled "Three Wire Headset," filed Jul. 11, 2003. The entire disclosure and contents of the above application is hereby incorporated by reference herein.

This application is related to U.S. Pat. Nos. 4,532,930, 6,537,200, 6,565,503, 6,575,894, and 6,697,674. The entire disclosure and contents of the above patents are hereby incorporated by reference herein.

BACKGROUND

1. Field of the Invention

The present invention relates generally to cabling and wiring arrangements and, more particularly, to cabling for transmitting signals between components of an implantable medical device.

2. Related Art

The use of medical devices to provide therapy to individuals for various medical conditions has become more widespread as the advantages and benefits such devices provide become more widely appreciated and accepted throughout the population. In particular, devices such as hearing aids, implantable pacemakers, defibrillators, functional electrical stimulation devices such as cochlear prostheses, organ assist or replacement devices, and other medical devices, have been successful in performing life saving and/or lifestyle enhancement functions for a number of individuals.

Many such medical devices often include one or more sensors, processors, controllers or functional electrical components that are permanently or temporarily implanted in a patient. Many such implantable devices require the transfer of power and/or information with external components that are part of, or operate in conjunction with, the implanted components of the medical device. One common approach to provide for the transcutaneous transfer of power and information with an implantable component is via a transcutaneous transfer system which couples patient-worn components with the implanted components.

One such type of medical device is a cochlear implant system. Cochlear implant systems provide the benefit of hearing to individuals suffering from severe to profound hearing loss. Hearing loss in such individuals is due to the absence or destruction of the hair cells in the cochlea which transduce acoustic signals into nerve impulses. Cochlear implants essentially simulate the cochlear hair cells by directly delivering electrical stimulation to the auditory nerve fibers. This causes the brain to perceive a hearing sensation resembling the natural hearing sensation normally delivered to the auditory nerve.

Conventional cochlear implant systems primarily include an external assembly directly or indirectly attached to the body of the patient (sometimes referred to herein as the recipient), and an internal assembly which is implanted in the patient. The external assembly typically comprises one or more microphones for detecting sound, a speech processing unit that converts detected sound into an electrical coded signal, a power source, and an external transcutaneous transfer coil. The internal assembly typically comprises an internal transcutaneous transfer coil, a stimulator unit located within a recess of the temporal bone of the recipient, and an electrode array positioned in the recipient's cochlear.

Collectively, the external transcutaneous transfer coil and the internal transcutaneous transfer coil form an inductively-coupled coil system of a transcutaneous transfer system. The transfer of energy via this system is controlled to effect the transmission of the electrical coded signals, referred to herein as stimulation signals, and power signals from the external speech processing unit to the implanted stimulator unit. Similarly, the transcutaneous transfer system may be used to effect the transmission of telemetry data from the implanted stimulator unit to the exterior speech processing unit. Conventionally, the communications link has been in the form of a radio frequency (RF) link, although other such links have been proposed and implemented. Once a stimulation signal has been transmitted to the implanted transcutaneous transfer coil, it is provided to the implanted stimulator unit which processes the signal and outputs one or more signals to the intra-cochlear electrode assembly which applies the electrical stimulation directly to the auditory nerve of the recipient.

There are two common arrangements of the noted external assembly components. In one arrangement, the microphone(s) is/are combined with the speech processing unit in a so-called "behind-the-ear" configuration. In such a configuration, the external coil is a separate unit connected to the speech processing unit via a cable. In the other common arrangement, at least one microphone is combined with the external transmission coil. If one or more additional microphones are included in the speech processing unit, then the speech processing unit is designed to be worn behind the ear and is connected to the external coil via a cable. On the other hand, if the speech processing unit does not include a microphone it may be designed to be worn on the body of the recipient and connected to a headset unit worn behind the ear via a cable. The headset, in turn is connected to the external coil via a second cable.

SUMMARY

In accordance with one aspect of the present invention, a cable for communicably connecting a first component and a second component of a cochlear implant system is disclosed. The cable comprises: a first conductor for conducting at least one analog-domain signal a second conductor for conducting at least one digital-domain signal; and at least one ground conductor electrically coupled to the first and second conductors.

In accordance with another aspect of the present invention, a medical device is disclosed. The medical device comprises: a first component; a second component; and a cable having a plurality of conductors each dedicated to the transmission of one or more signals between the first and second components, wherein the one or more signals transmitted over each of the plurality of conductors are all either an analog-domain signal, a digital-domain signal, or a ground signal.

In accordance with a further aspect of the present invention a method for transmitting signals between a first and second component of a medical device is disclosed. The method comprises: transmitting at least one analog-domain signal over a first conductor of the cable; and transmitting at least one digital-domain signal over a second conductor of the cable.

DETAILED DESCRIPTION

Embodiments of the present invention are directed to a cable having a plurality of conductors each dedicated to the transmission of one or more signals between external components of a medical device, and method for using the same. The one or more signals which are transmitted over each individual conductor of the cable are all either analog-domain signal(s), digital-domain signal(s), or ground signal(s). When more than one signal is transmitted over a single conductor, the implemented transmission technique preferably facilitates the differentiation of such signals. For example, analog signals may be modulated while digital signals may be time- or frequency-multiplexed.

Such analog-domain/digital-domain separation across conductors reduces cross-talk between such signals without having to transmit each signal over a dedicated conductor that is separately shielded from other conductors in the cable. Consequently, the cable of the present invention is more reliable, flexible, lighter and of significantly smaller diameter than conventional cables traditionally utilized to transmit analog and digital signals.

The cabling of the present invention is particularly beneficial for transmitting analog and digital signals between external components of an implantable medical device. Such components are worn on the body of a recipient, often for considerable periods of time and during various activities ranging from the sedentary to the active. The minimal dimensions and increased flexibility of such cabling improves the aesthetics of the medical device, facilitating a reduction in self-consciousness of the recipient, while improving the freedom of movement and comfort of the recipient.

Embodiments of the present invention are described below in connection with one embodiment of an exemplary implantable medical device, a cochlear prosthesis (also referred to as a cochlear implant system, cochlear prosthetic device and the like). Cochlear prostheses use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a cochlear prosthetic device provides stimulation of the cochlear nucleus in the brainstem.

Figure 1:
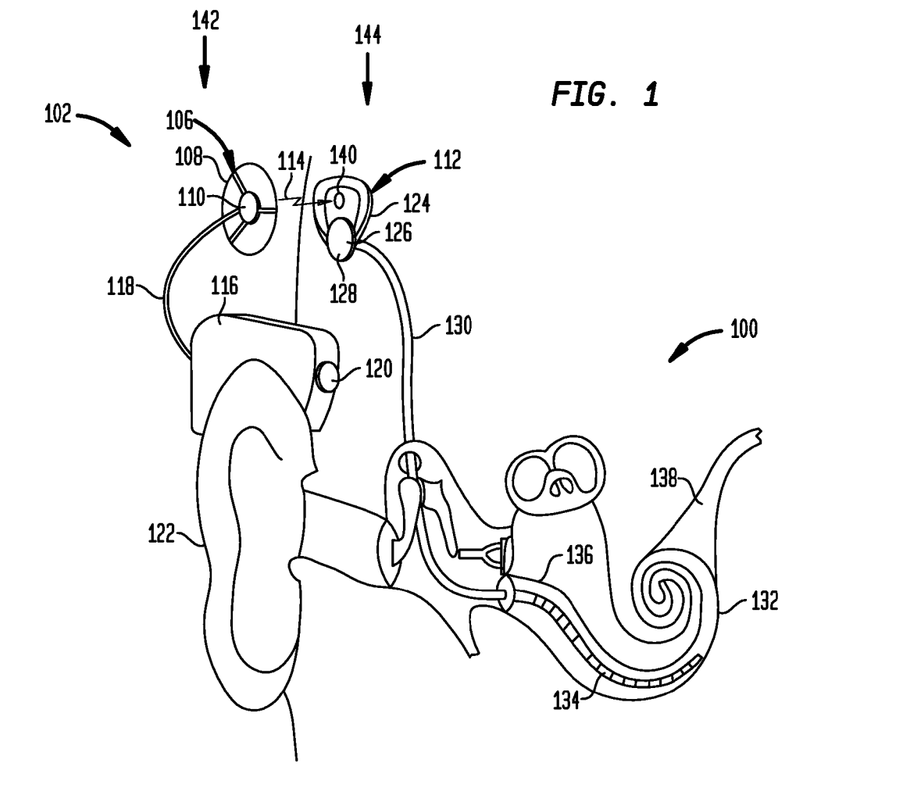
FIG. 1 is a simplified perspective view of internal and external components of an exemplary cochlear implant system shown in their operational position on a recipient.

Exemplary cochlear prostheses in which the present invention may be implemented include, but are not limited to, those systems described in U.S. Pat. Nos. 4,532,930, 6,537,200, 6,565,503, 6,575,894 and 6,697,674, which are hereby incorporated by reference herein. FIG. 1 is a schematic diagram of an exemplary cochlear implant system 100 in which embodiments of the present invention may be implemented. Cochlear implant system 100 comprises external component assembly 142 which is directly or indirectly attached to the body of the recipient, and an internal component assembly 144 which is temporarily or permanently implanted in the recipient. External assembly 142 typically comprises audio pickup devices 120 for detecting sound, a speech processing unit 116 a power source (not shown), and an external transmitter unit 106. External transmitter unit 106 comprises an external coil 108, and preferably, a magnet 110 secured directly or indirectly to external coil 108. Speech processing unit 116 processes the output of audio pickup devices 120 that are positioned, in the depicted embodiment, by the ear 122 of the recipient. Speech processing unit 116 generates coded signals, referred to herein as a stimulation data signals, which are provided to external transmitter unit 106 via cable 118.

Internal components 144 comprise an internal receiver unit 112, a stimulator unit 126, and an electrode array 134. Internal receiver unit 112 comprises an internal transcutaneous transfer coil 124, and preferably, a magnet 140 fixed relative to internal coil 124. Internal receiver unit 112 and stimulator unit 126 are hermetically sealed within a housing 128. Internal coil 124 receives power and data from external coil 108, as noted above. A cable 130 extends from stimulator unit 126 to cochlea 132 and terminates in electrode array 134. Signals generated by stimulator unit 126 are applied by array 134 to the basilar membrane 136, thereby stimulating the auditory nerve 138.

Collectively, transmitter antenna coil 108 (or more generally, external coil 108) and receiver antenna coil 124 (or, more generally internal coil 124) form an inductively-coupled coil system of a transcutaneous transfer apparatus 102. In one embodiment, external coil 108 transmits electrical signals to internal coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone moulding (not shown). In use, implantable receiver unit 112 may be positioned in a recess of the temporal bone adjacent ear 122 of the recipient.

Figure 2A:
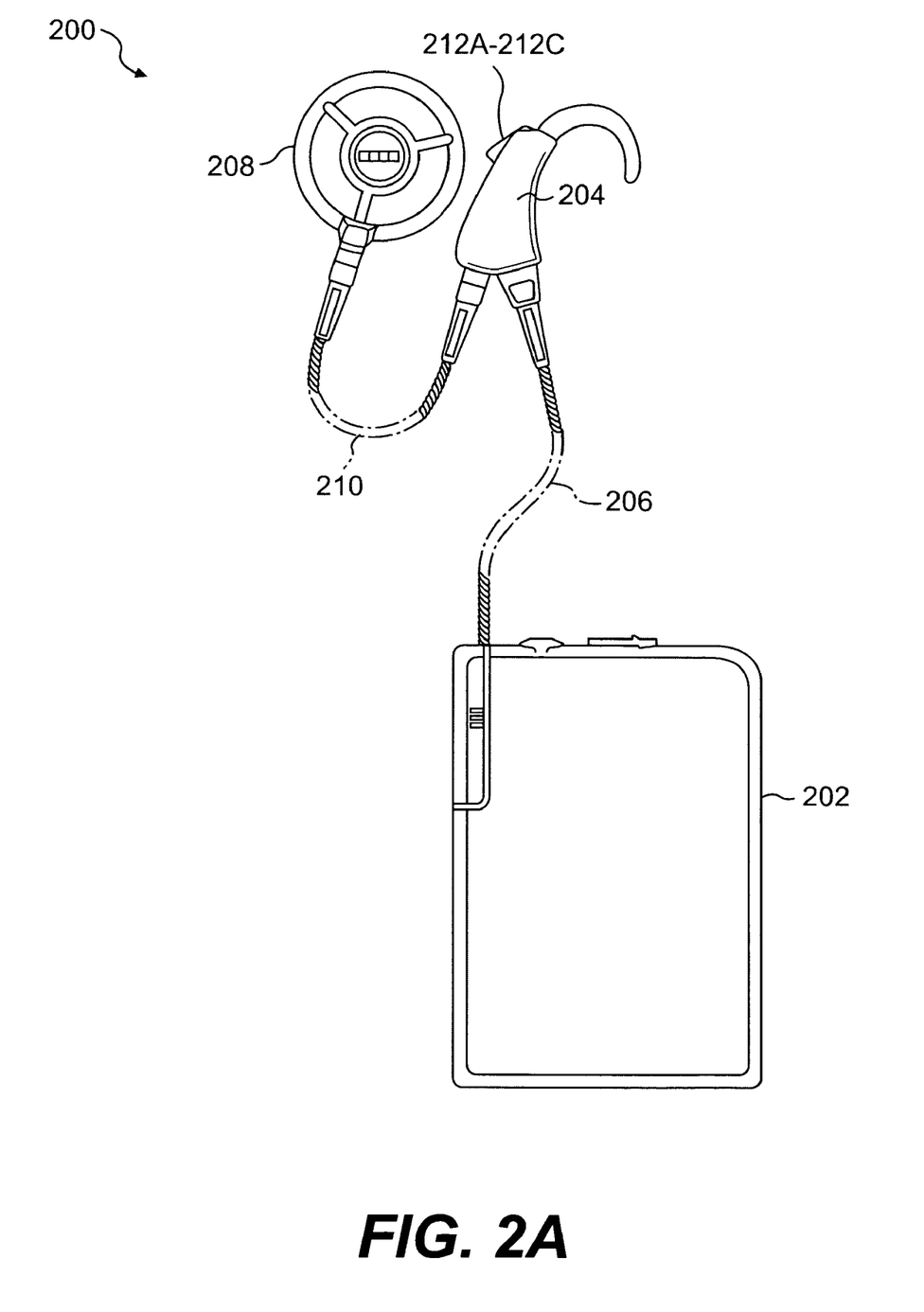
FIG. 2A is a perspective view of the external components of the cochlear implant system shown in FIG. 1, according to one embodiment of the present invention.

External assembly 142 of cochlear implant system 100 may have different configurations and arrangements. FIG. 2A is a perspective view of one embodiment of external assembly 142, referred to as external assembly arrangement 200. In arrangement 200, a body-worn speech processing unit 202 is connected to a headset unit 204 with a first cable 206. Headset unit 204 is, in turn, connected to a transmitter coil 208 with a second cable 210.

In this exemplary embodiment, headset unit 204 comprises three audio pickup devices 212A, 212B and 212C (collectively and generally referred to herein as audio pickup device or devices 212). In one embodiment, audio pickup devices 212 are microphones, although in alternative embodiments audio pickup devices 212 can be telecoils or other similar devices now or later developed. Each audio pickup device 212 detects and converts ambient sound into an electrical audio signal. The electrical audio signals are transmitted over cable 206 to speech processing unit 202, which contains appropriate speech processing circuitry to convert the electrical audio signals into electrical coded stimulation signals according to a particular speech processing strategy. The stimulation signals are transmitted via cable 206 from speech processing unit 202 to headset unit 204, and from headset unit 204 to external coil 208 via cable 210, for transmission over an RF link to implanted stimulator unit 126 (FIG. 1).

Figure 2B:
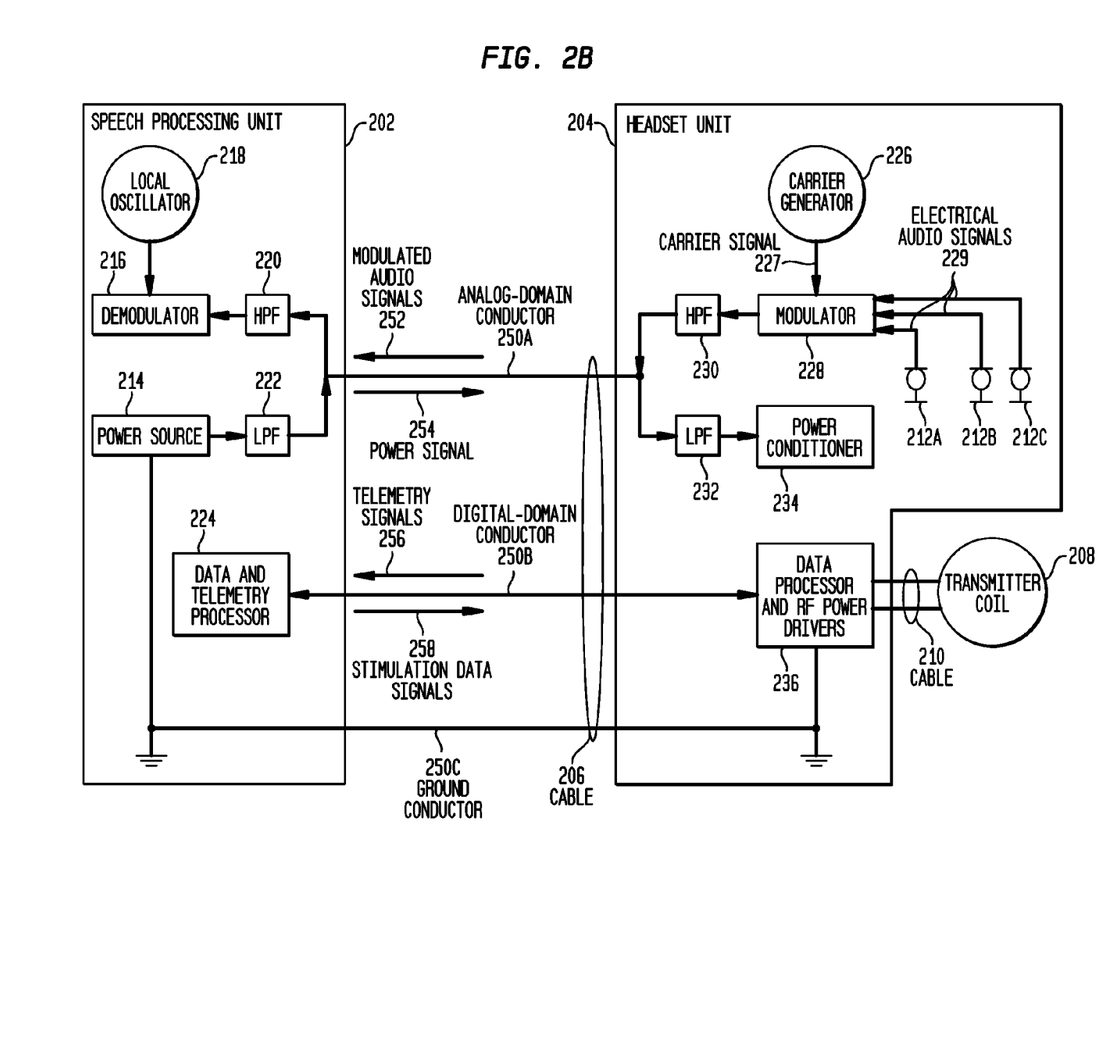
FIG. 2B is an interface block diagram of the components of illustrated in FIG. 2A, in accordance with one embodiment of the present invention.

FIG. 2B is a simplified block diagram of external assembly 200 illustrated in FIG. 2A. In FIG. 2B the primary components of speech processing unit 202 and headset unit 204 are depicted, along with external coil 208. Generally, speech processing unit 202 comprises a power source 214, a demodulator 216, oscillator 218, high pass filter 220, low pass filter 222 and a data/telemetry processor 224, operably coupled as shown in FIG. 2B and described below. Headset unit 204 comprises the noted audio input sources 212, a carrier generator 226, modulator 228, high pass filter 230, low pass filter 232, power conditioner 234, and a data processor/RF power driver 236 all operably coupled as shown in FIG. 2B and described below.

As noted, cable 206 is connected to speech processing unit 202 and headset unit 204 while cable 210 connects headset unit 204 to transmitter coil 208. In the embodiment shown in FIG. 2B, cable 206 comprises a plurality of conductors 250A, 250B and 250C (collectively and generally referred to herein as conductor or conductors 250). Conductor 250A is dedicated to conducting analog-domain signals and is referred to herein as analog-domain conductor 250A. Similarly, conductor 250B is dedicated to conducting digital-domain signals and is referred to herein as digital-domain conductor 250B. Cable 206 comprises at least one ground conductor to provide shielding for the transmitted signals. In the exemplary embodiment shown in FIG. 2B, a single ground conductor 250C is included in cable 206.

In the exemplary embodiment shown in FIG. 2B, analog-domain conductor 250A is utilized to transmit modulated audio signals 252 from headset unit 204 to speech processing unit 202, and to concurrently transmit power signal 254 from speech processing unit 202 to headset unit 204. Each of these analog-domain signals is described next below.

The transmission of audio information between headset unit 204 and speech processing unit 202 begins first with the use of multiple audio pickup devices 212. Devices 212, together with a programmable modulator/encoder 228 allows the transmission of a number of audio signals from the different pick-up sources to the speech processor. These signals can be simultaneously processed by the speech processor to achieve the best possible signal/background noise ratio an best directivity. This is done using beamforming and noise identification and reduction signal processing methods that are known today or may be developed in the future. As is well-known in the art, beamforming requires delaying the electrical audio signal generated by a first audio pickup device 212 with the time that the sound needs to travel from the first audio pickup device 212 to a second audio pickup device 212.

Carrier generator 226 generates a high frequency carrier signal 227 which is provided to modulator 228. The electrical audio signals 229 generated by audio pickup devices 212 together modulate high frequency carrier signal 227. The modulated audio signals 252 are then transmitted from headset unit 204 via high pass filter 230 and analog-domain conductor 250A.

Speech processing unit 202 receives modulated audio signals 252 via a high pass filter 220. The filtered modulated audio signals 252 are demodulated at demodulator 216 using a local oscillator 218. The modulation and demodulation of one or more electrical audio signals 229 is well-known to those of ordinary skill in the relevant art and, therefore, is not described further herein.

As noted, power signal 254 is also conducted by analog-domain conductor 250A. Power source 214 in speech processing unit 202 transmits power signal 254 to headset unit 204 over analog-domain conductor 250A via low pass filter 222 in speech processing unit 202. Power conditioner 234 in headset unit 204 receives power signal 254 from speech processing unit 202 via low pass filter 232. The resulting power is thereafter used to power headset unit 204, as is well-known in the art. Preferably, the power is delivered using alternating current (ac) because such power transmission has the advantage of reducing corrosion at the cable connector pins (not shown), which is more likely to occur in humid environments.

Hence, in the embodiment shown in FIG. 2B, power signal 254 and modulated audio signals 252 are concurrently transmitted between speech processing unit 202 and headset unit 204 over a single conductor 250A dedicated to conducting such and other analog-domain signals between such components.

In the exemplary embodiment shown in FIG. 2B, digital-domain conductor 250B is utilized to transmit telemetry feedback signals 256 from implanted headset unit 204 to external speech processing unit 202, and to concurrently transmit stimulation data signals 258 from speech processing unit 202 to headset unit 204. Each of these digital-domain signals is described next below.

Speech processing unit 202 includes, as noted, data and telemetry processor 224. Processor 224 converts the detected sounds provided by demodulator 216 into electrical coded signals referred to herein as stimulation signals 258. Stimulation signals 258 are transmitted to headset unit 204 via digital-domain conductor 250B. Headset unit 204 comprises, as noted, data processor/RF power drivers 236 that receive stimulation signals 258, and which drives transmitter coil 208 accordingly to control the transfer of energy to implanted stimulator unit 126.

One of the continuing developments made to improve the functionality of implantable medical devices such as cochlear implant system 100, is the broader utilization of telemetry. Telemetry data provides a clinician, engineer, researcher, etc. with information regarding, for example, the implanted electrode array 134, stimulator unit 126 and other components of implantable assembly 144. Such data may include, for example, operational, diagnostic, status and other information regarding the components of implantable assembly 144. In the context of cochlear implant systems, such telemetry data may include information regarding, for example, electrode impedance, compliance voltage, stimulator unit status, etc. In alternative embodiments, such data may also include recipient data obtained through sensors included in implantable assembly 144. Such recipient data may include, for example, blood flow rate, blood pressure, pH, temperature and other physiological parameters. In the context of cochlear implant systems, such telemetry data may include information regarding, for example, recordings of neural response. The above and other data which may be generated by an implantable medical device now or later developed, is generally and collectively referred to herein as telemetry data.

Telemetry data is received by external coil 208 and transmitted to data processor/power drivers 236 via cable 210. These data signals are processed by data processor/RF power driver 236, and communicated to speech processing unit 202 as telemetry feedback signals 256. Data and telemetry processor 224 of speech processing unit 202 receives and processes telemetry signals 256 and stores, outputs or otherwise utilizes the received telemetry data, as is well-known in the art.

Hence, in the embodiment shown in FIG. 2B, telemetry feedback signals 256 and stimulation data signals 258 are concurrently transmitted between speech processing unit 202 and headset unit 204 over a single conductor 250B dedicated to the transfer of such and other digital-domain signals. Preferably, the implemented transmission techniques facilitate the differentiation of digital-domain signals conducted over digital-domain conductor 250B. For example, such digital signals may be time- or frequency-multiplexed.

The above analog- and digital-domain signal allocation among conductors 250 of cable 206 reduces the shielding required or desired to be provided in cable 206. Such shielding can be provided by one or more ground conductors. Such ground conductors can provide either a common or isolated ground for each signal conductor in cable 206.

In the embodiment shown in FIG. 2B, for example, a single ground conductor 250C is included in cable 206. Ground conductor 250C is shared by analog-domain conductor 250A and digital-domain conductor 250B. In signal processing unit 202, ground conductor 250C is connected to the ground terminal of power source block 214 while in headset unit 204 ground conductor 250C is connected to the ground terminal of data processor/RF power drivers 236. It should be appreciated by those of ordinary skill in the art, however, that an additional ground conductor may be included in cable 206. In such an embodiment, one ground conductor is connected to only analog-domain conductor 250A while the other ground conductor is connected to only to digital-domain conductor 250B.

Figure 3A:
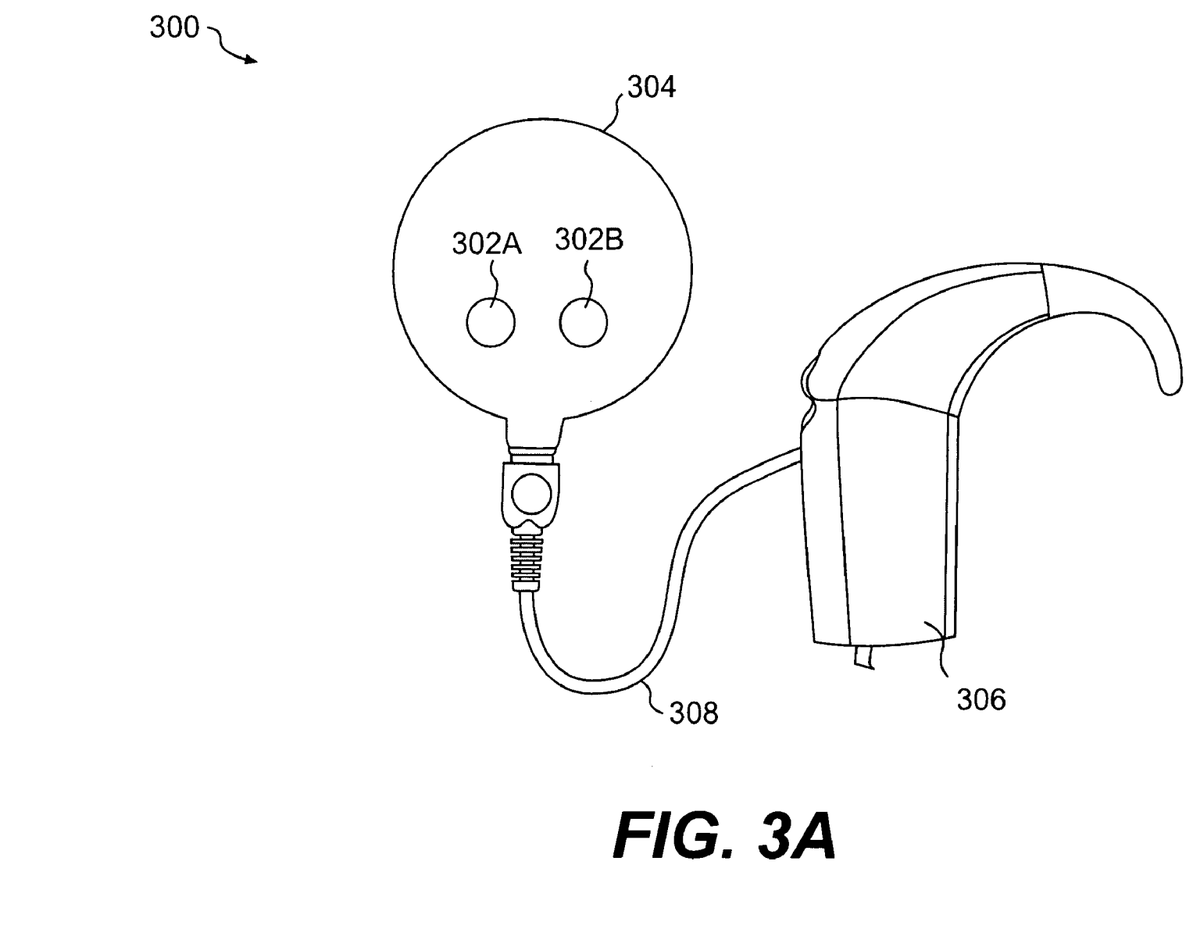
FIG. 3A is a perspective view of the external components of the cochlear implant system shown in FIG. 1, according to one embodiment of the present invention.

As noted, external assembly 142 may be implemented in different configurations. FIG. 3A is a perspective view of an arrangement 300 of external assembly 142 similar to that shown in FIG. 1.

Arrangement 300 is operationally similar to arrangement 200, except that two audio pickup devices 302A, 302B (collectively and generally referred to herein as audio pickup device or devices 302) are provided, rather than the three devices 212 implemented in the embodiment shown in FIGS. 2A-2B. Devices 302 are installed together in a transmitter coil unit 304, which is connected to a speech processing unit 306 via a cable 308. As shown in FIG 3A, speech processing unit 306 is configured to fit behind the ear of the recipient.

Figure 3B:
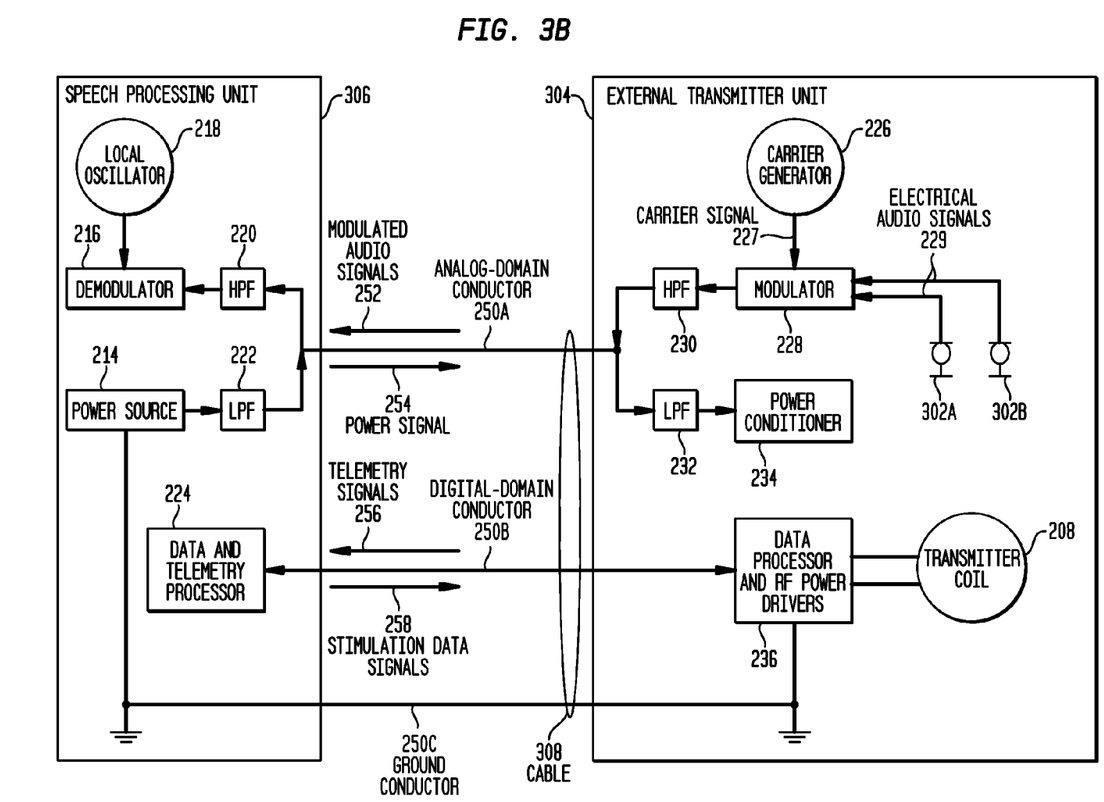
FIG. 3B is an interface block diagram of the components of illustrated in FIG. 3A, in accordance with another embodiment of the present invention.

Referring to FIG. 3B, external assembly 300 of cochlear implant system 100 is functionally similar to the architecture of external assembly 200 introduced above in connection with FIG. 2B. Accordingly, like reference numerals in FIGS. 2B and 3B designate the same or similar components. As shown in FIG. 3B, cable 308 communicably couples speech processing unit 306 and external transmitter unit 304, and contains conductors 250A-250C which are the same as the conductors of cable 206 described above in connection with FIGS. 2A-2B. Similarly, such conductors in FIG. 3B conduct the same signals as those described above with reference to the embodiment presented in FIGS. 2A-2B.

It will be appreciated by persons skilled in the art that numerous variations and/or modifications may be made to the invention as shown in the specific embodiments without departing from the spirit or the scope of the invention as broadly described. As one example, the present invention has been described in the context of a cochlear implant system. However, as noted, the present invention can be implemented in any implantable medical device now or later developed. As another example, in the above embodiment, the cabling system of the present invention was utilized to connect two external components of a cochlear implant system. It should be appreciated, however, that the teachings of the present invention may be implemented to provide communications between two internal components of an implantable medical device, or to provide communications between an internal and an external of an implantable medical device. The present embodiments are, therefore, to be considered in all respects as illustrative and not restrictive.

What is claimed is:

1. A method for conducting signals in a medical device, the medical device comprising first and second components, an implantable component, and a cable having a first conductor, a second conductor and at least one ground conductor electrically coupled to said first and second components, the method comprising:
   conducting only analog-domain signals between said first and second components over the first conductor, comprising: conducting a power signal from the first component to the second component;
   conducting only digital-domain signals between said first and second components over the second conductor, comprising: conducting at least one telemetry feedback signal;
   conducting a ground signal between said first and second components over the at least one ground conductor; and
   transmitting the power signal to the implantable component.

2. The method of claim 1, wherein said medical device is a cochlear implant system.

3. The method of claim 1, wherein said first and second components are external components of said medical device configured to be externally worn.

4. The method of claim 1, wherein said conducting only analog-domain signals further comprises:
   conducting at least one audio signal.

5. The method of claim 4, wherein said conducting the at least one audio signal comprises:
   modulating one or more of the at least one audio signal.

6. The method of claim 1, wherein said conducting only digital-domain signals further comprises:
   multiplexing a plurality of the digital-domain signals.

7. The method of claim 1, wherein said conducting only digital-domain signals further comprises:
   conducting at least one stimulation data signal.

8. The method of claim 1, wherein said conducting only analog-domain signals further comprises:
   concurrently conducting two or more of the analog-domain signals.

9. The method of claim 1, further comprising:
   modulating each of two or more of the analog-domain signals.

10. The method of claim 1, wherein said conducting only digital-domain signals further comprises:
    concurrently conducting two or more of the digital-domain signals.

11. A method for conducting signals in a medical device, the medical device comprising first and second components, an implantable component, and a cable having a first conductor, a second conductor and at least one ground conductor electrically coupled to said first and second components, the method comprising:
    conducting only analog-domain signals between said first and second components over the first conductor, comprising: conducting a power signal from the first component to the second component;
    conducting only digital-domain signals between said first and second components over the second conductor, comprising: conducting at least one stimulation data signal;
    conducting a ground signal between said first and second components over the at least one ground conductor; and
    transmitting the power signal to the implantable component.

12. The method of claim 11, wherein said medical device is a cochlear implant system.

13. The method of claim 11, wherein said first and second components are external components of said medical device configured to be externally worn.

14. The method of claim 11, wherein said conducting only analog-domain signals further comprises:

conducting at least one audio signal.

15. The method of claim 14, wherein said conducting the at least one audio signal further comprises:

modulating one or more of the at least one audio signal.

16. The method of claim 11, wherein said conducting only digital-domain signals further comprises:

multiplexing a plurality of the digital-domain signals.

17. The method of claim 11, wherein said conducting only analog-domain signals further comprises:

concurrently conducting two or more of the analog-domain signals.

18. The method of claim 11, further comprising:

modulating each of two or more of the analog-domain signals.

19. The method of claim 11, wherein said conducting only digital-domain signals further comprises:

concurrently conducting two or more of the digital-domain signals.

20. A method for conducting signals in a medical device, the medical device comprising first and second components, an implantable component, and a cable having a first conductor, a second conductor and at least one ground conductor electrically coupled to said first and second components, the method comprising:

conducting only analog-domain signals between said first and second components over the first conductor, comprising: conducting a power signal from the first component to the second component;

conducting only digital-domain signals between said first and second components over the second conductor, comprising: concurrently conducting two or more of the digital-domain signals;

conducting a ground signal between said first and second components over the at least one ground conductor; and transmitting the power signal to the implantable component.

21. The method of claim 20, wherein said medical device is a cochlear implant system.

22. The method of claim 20, wherein said first and second components are external components of said medical device configured to be externally worn.

23. The method of claim 20, wherein said conducting only analog-domain signals comprises:

conducting at least one audio signal.

24. The method of claim 23, wherein said conducting the at least one audio signal comprises:

modulating one or more of the at least one audio signal.

25. The method of claim 20, wherein said conducting only digital-domain signals comprises:

multiplexing a plurality of the digital-domain signals.

26. The method of claim 20, wherein said conducting only analog-domain signals further comprises:

concurrently conducting two or more of the analog-domain signals.

27. The method of claim 20, further comprising:

modulating each of two or more of the analog-domain signals.

* * * * *